(12) United States Patent  (10) Patent No.: US 8,781,072 B2
Robinson  (45) Date of Patent: Jul. 15, 2014

(54) APPARATUS AND METHOD FOR CHARACTERISATION OF MATERIALS

(75) Inventor: Max Robinson, Shincliffe (GB)

(73) Assignee: Kromek Limited, Durham (GB)

( * ) Notice: Subject to any disclaimer, the term of this patent is extended or adjusted under 35 U.S.C. 154(b) by 411 days.

(21) Appl. No.: 13/140,491

(22) PCT Filed: Dec. 14, 2009

(86) PCT No.: PCT/GB2009/051705
§ 371 (c)(1),
(2), (4) Date: Aug. 31, 2011

(87) PCT Pub. No.: WO2010/070327
PCT Pub. Date: Jun. 24, 2010

(65) Prior Publication Data
US 2011/0305318 A1    Dec. 15, 2011

(30) Foreign Application Priority Data
Dec. 19, 2008    (GB) .................................. 0823093.0

(51) Int. Cl.
    *G01N 23/201*    (2006.01)
(52) U.S. Cl.
    USPC .......................................................... 378/88
(58) Field of Classification Search
    USPC .............................................. 378/57, 70–88
    See application file for complete search history.

(56) References Cited

U.S. PATENT DOCUMENTS

| 4,228,351 A | 10/1980 | Snow et al. |
| 4,799,247 A | 1/1989 | Annis et al. |
| 5,313,511 A | 5/1994 | Annis et al. |
| 5,943,388 A | 8/1999 | Tumer |
| 5,974,111 A | 10/1999 | Krug et al. |
| 5,313,511 C1 | 1/2001 | Annis et al. |
| 6,256,372 B1 | 7/2001 | Aufrichtig et al. |
| 6,285,482 B1 | 9/2001 | Date |
| 6,661,867 B2 | 12/2003 | Mario et al. |

(Continued)

FOREIGN PATENT DOCUMENTS

| CN | 1979140 A | 12/2005 |
| EP | 0261984 | 3/1988 |

(Continued)

OTHER PUBLICATIONS

XP-001025166—Strecker, H.: "Simulation-Based Training and Testing of Classification Schemes for CXRS Explosives Detection", Philips Research Laboratories, Technical Systems Department, 88/SPIE vol. 2511, Jun. 21, 1995, pp. 88-98.

(Continued)

*Primary Examiner* — Courtney Thomas
(74) *Attorney, Agent, or Firm* — Drinker Biddle & Reath LLP

(57) ABSTRACT

An apparatus and method are described for obtaining radiation interaction data from an object to enable better determination of the composition of the object. A radiation source and a radiation detector system are used to collect both transmitted and scattered radiation, preferably including radiation from at least one forward scatter mode. The detector system is capable of detecting and collecting spectroscopically resolvable information about incident radiation. Each intensity dataset is resolved across at least three of energy bands within the spectrum of the source, and this data may then be processed numerically to enable better determination of the composition of the object.

21 Claims, 5 Drawing Sheets

(56) References Cited

U.S. PATENT DOCUMENTS

| | | |
|---|---|---|
| 7,362,847 B2 | 4/2008 | Bijjani |
| 2003/0231739 A1 | 12/2003 | Rosner |
| 2006/0078085 A1 | 4/2006 | Zanker |
| 2008/0008292 A1 | 1/2008 | Krmar et al. |
| 2008/0205583 A1 | 8/2008 | Seppi et al. |
| 2008/0219404 A1 | 9/2008 | Moore |
| 2008/0240356 A1* | 10/2008 | Robinson .................... 378/98.2 |
| 2008/0283761 A1 | 11/2008 | Robinson et al. |

FOREIGN PATENT DOCUMENTS

| | | |
|---|---|---|
| EP | 0610084 | 4/1998 |
| GB | 1531755 | 11/1978 |
| GB | 2329817 | 3/1999 |
| GB | 2360685 | 9/2001 |
| GB | 2390005 | 12/2003 |
| JP | 01-172739 | 7/1989 |
| JP | 04-258784 | 9/1992 |
| JP | 04-319654 | 10/1992 |
| JP | 2641208 | 5/1997 |
| JP | 11-14336 | 1/1999 |
| WO | 9833063 | 7/1998 |
| WO | 2005059594 | 6/2005 |
| WO | WO 2006/010056 A2 | 1/2006 |
| WO | 2007070580 | 6/2007 |
| WO | WO 2008/060667 A2 | 5/2008 |
| WO | 2008127385 A2 | 10/2008 |

OTHER PUBLICATIONS

International Search Report, dated May 7, 2010, 4 pages.
Written Opinion of the International Search Report, dated May 7, 2010, 6 pages.
Search Report for Application No. GB0823093.0, dated Mar. 11, 2009, 2 pages.
Wang et al., "Stereoscopic dual-energy X-ray imaging for target materials identification", Vision, Image and Signal Processing, IEE Proceedings, vol. 150, No. 2, Apr. 21, 2003, pp. 122-130.
Hon et al., "Multiple-view line-scan imaging, Optoelectronics", IEE Proc., vol. 149, No. 2, Apr. 2002, pp. 45-50.
Evans et al., "Color 3D X-Ray Imaging for Security Screening", Crime and Security, 2006, The Institution of Engineering and Technology Conference, Jun. 13-14, 2006, pp. 372-377.
Evans, "Kinetic depth effect X-ray (KDEX) imaging for security screening", Visual Information Engineering, 2003, VIE 2003. International Conference, Jul. 7-9, 2003, pp. 69-72.
Evans et al., "Depth from motion 3D X-ray imaging for security screening", Imaging for Crime Detection and Prevention, 2005 (ICDP), The IEE International Symposium, Jun. 7-8, 2005, pp. 5-8.
Evans, "Stereoscopic imaging using folded linear dual-energy x-ray detectors", Meas. Sci. Technol. 13, pp. 1388-1397 (2002).
JP Office Action, 2011-541594, Aug. 13, 2013, 9 pages (including translation and identifying pertinence of cited references).
Japanese Office Action, dated Apr. 22, 2014, 2 pages.

* cited by examiner

APPARATUS AND METHOD FOR CHARACTERISATION OF MATERIALS

FIELD OF THE INVENTION

The invention relates to an apparatus and method for the characterisation of materials.

The invention in particular relates to an apparatus and method making use of high energy radiation such as x-rays or gamma-rays to scan objects where it is desirable to gain information about their internal contents and/or composition.

The invention is useful in particular in relation to circumstances where it might be desirable to gain information about the internal contents and/or composition of an object, for example including an object comprising multiple component elements or materials, contained liquid or liquid sample etc, for example for identification purposes, for stock control or quality control purposes, to monitor changes and especially degradation over time, in a security or like situation for the detection of dangerous or prohibited materials, for example to screen baggage for entry into or exit from a restricted area.

BACKGROUND

X-ray absorption has been used as the basis for screening objects both to create some form of representational image of the contents or components thereof relative to each other in three-dimensional space and to obtain some indication of likely composition. The thicker or more dense an object is then the more it will attenuate an x-ray beam. By use of suitable detectors and a suitable source, radiographs of an item under screening in the form of images based on the absorption of an object or set of objects can be generated.

It is known that spectroscopic information from transmitted x-rays could be used to give additional information about the material content of the objects or components being scanned. It is known that the x-ray absorption properties of any material can vary spectroscopically, and that this effect depends in particular on atomic number. This has led to development of dual-band or dual-energy detectors which are capable of separately identifying low- and high-energy bands from the full spectrum of x-ray emissions. More recently, the development of detectors that can resolve spectroscopic information about the transmitted x-rays more effectively has led to the development of apparatus that discriminate across a larger range of bands and generate a larger plurality of images. For example U.S. Pat. No. 5,943,388 describes a system that makes use of cadmium telluride detectors to image across at least three energy bands and generate at least three images.

Such systems allow the presentation of transmission radiographs with spectroscopic energy resolution, which can assist in the declutter of extraneous information relative to that presented in broad spectrum monochromatic images presenting merely average intensity across the spectrum, especially where an object comprises multiple component elements or materials in the transmission path. They do not always collect data in such a way as to allow derivation of characteristic material information. It is desirable to do so more effectively.

Even with this resolution, such devices can still be confused by objects which are superimposed in the x-ray path. Moreover, they generally will give no information concerning the crystalline or polycrystalline nature of an object.

Polycrystalline materials scatter x-rays and, the resulting x-ray image may hardly detect such polycrystalline material because a very large portion of the x-rays which have not been absorbed by the material will have been scattered and so not received by the detector. This is unfortunate as in security x-ray screening a number of threat items are polycrystalline in nature, in particular plastic explosives such as CP4, RDX, PETN and proprietary formulations thereof, drugs and the like and are therefore difficult to detect by using conventional x-ray systems.

U.S. Pat. No. 5,313,511 outlines a system for producing separate images for the transmitted beam detected using dual energy detectors, the backscattered beam and the forward scattered beam. The forward and back scattered beam images contain only intensity information and cannot be combined with the transmission image for more accurate imaging and materials identification.

SUMMARY OF THE INVENTION

According to one aspect of the invention there is provided an apparatus for obtaining radiation interaction data from an object to determine information about the composition of the object comprising:

a radiation source and a radiation detector system spaced therefrom to define a scanning zone therebetween and to collect in use information about radiation incident at the detector system after interaction with an object in the scanning zone, the detector system being capable of detecting and collecting spectroscopically resolvable information about incident radiation;

wherein the radiation detector system comprises a first detector means positioned to collect a first intensity dataset of radiation incident thereupon after transmission through an object, and at least one further detector means positioned to collect a further intensity dataset radiation incident thereupon after a scattering interaction with an object;

and wherein the apparatus further comprises a first data processing module adapted to resolve said first intensity dataset across at least three energy bands within the spectrum of the source, and at least one further data processing module adapted to resolve said further intensity dataset across at least three energy bands within the spectrum of the source.

In accordance with the invention a transmission dataset and at least one further scattered dataset are processed by being spectroscopically resolved across at least three energy bands within the spectrum of the source to determine information about the composition of the object. The further scattered dataset particularly preferably comprises a dataset of forward scattered intensity data, collected by a suitable further detector. The forward scattered intensity data may for example be coherently scattered intensity data and/or incoherently scattered intensity data.

In a possible embodiment, plural further datasets may be collected of plural coherent and/or incoherent forward and/or back scattered modes. For example, plural further detector means may be positioned to collect plural further intensity dataset radiation incident thereupon after plural different scattering interactions with an object, each such intensity dataset being processed by a further data processing module as above described. In such a case at least one of the plural further datasets is preferably a dataset of forward scattered intensity data. The forward scattered intensity data may for example be coherently scattered intensity data and/or incoherently scattered intensity data.

The detector system is capable of detecting and collecting spectroscopically resolvable information about incident radiation in the sense that it is adapted to differentiate incident radiation simultaneously into plural separate energy bands across the spectrum of the source. For example, the detector system exhibits a spectroscopically variable response across at least a part of the source spectrum allowing such simultaneous differentiation of incident radiation into plural energy bands. The data processing modules are adapted to exploit this feature of the system so as each to resolve the resultant intensity dataset into at least three such energy bands across the spectrum of the source.

In accordance with the invention a first detector means is positioned to collect a first intensity dataset of transmitted radiation and at least one further detector means is positioned to collect a further intensity dataset of scattered, preferably forward scattered intensity data. The forward scattered intensity data may be collected from coherently forward scattered radiation and/or incoherently scattered radiation.

This captures more relevant information than that by just using the information provided by absorption (transmission) alone, even when spectrally resolved across at least three energy bands. By combining that data with scattered data, which is known to exist, and which is also spectrally resolved across at least three energy bands, more information is available in order to identify the material of interest. Both the scattered data and the transmitted data are spectrally significant in this regard. Combining the transmitted data with either the forward scatter or the back scatter or even combining all three (all of which are spectrally resolved) provides a better methodology for material identification.

Plural scattering datasets may be collected. Further scattering datasets may include forward scatter and/or back scatter. For some applications it might be desirable to use transmission and a single scatter mode such as a single forward scattered alone, for other applications transmission with multiple forward scatter modes and for some applications transmission with forward and back scatter. Examples are discussed below having these capabilities, but the generality of the invention is not limited thereby.

Thus, according to a preferred embodiment of the invention there is provided an apparatus for obtaining radiation interaction data from an object to determine information about the composition of the object comprising:
  a radiation source and a radiation detector system spaced therefrom to define a scanning zone therebetween and to collect in use information about radiation incident at the detector system after interaction with an object in the scanning zone, the detector system being capable of detecting and collecting spectroscopically resolvable information about incident radiation;
  wherein the radiation detector system comprises a first detector means positioned to collect a first intensity dataset of radiation incident thereupon after transmission through an object, a second detector means positioned to collect a second intensity dataset of radiation incident thereupon after forward scattering interaction with an object, and a third detector means positioned to collect a third intensity dataset of radiation incident thereupon after backward scattering interaction with an object;
  and wherein the apparatus further comprises a first data processing module adapted to resolve said first intensity dataset across at least three energy bands within the spectrum of the source,
  and a second data processing module adapted to resolving said second intensity dataset across at least three energy bands within the spectrum of the source,
  and a third data processing module adapted to resolving said third intensity dataset across at least three energy bands within the spectrum of the source.

Advantageously, the apparatus of the invention is able to generate for a given object, and for example simultaneously or closely successively, intensity data for both transmitted radiation and radiation scattered to at least one scatter detector position and to resolve such data into a plurality of energy bins. Both absorption of incident radiation and scattering of incident radiation are characteristic material behaviour that can vary characteristically with energy.

Although the invention is not limited by specific theory of operation, material interactions with ionizing radiation are well known with good predictive tools available in the literature and on the internet for carefully controlled system geometries. For photons with energy of between 10 keV and 160 keV the main contributing physical processes are the photoelectric effect, Thompson (coherent) scattering and Compton (incoherent) scattering. For many materials Compton (incoherent) scattering will be a particularly important forward scatter mode, It follows that it is in principle possible to analyse either or both energy-resolved intensity datasets numerically and obtain from such analysis information characteristic of the behaviour of the material(s) comprising an object under test or a component thereof which can be linked to and give information about the composition of the object under test.

Accordingly in a more complete preferred embodiment the first data processing module may further comprise an analysis module to analyse the energy-resolved first dataset across at least some of the resolved energy bands and to derive numerically therefrom information characteristic of the radiation absorption behaviour of the object under test and/or of material(s) comprising an object under test. Similarly the further data processing module(s) may further comprise analysis module(s) to analyse the energy-resolved further dataset(s) across at least some of the resolved energy bands and to derive numerically therefrom information characteristic of the radiation scattering behaviour of the object under test and/or of material(s) comprising an object under test.

The intensity datasets for the transmitted radiation, and for the at least one mode of scattered radiation, preferably including forward scattered radiation and for example in the preferred case forward scattered radiation and back scattered radiation, are preferably resolved into respective plural energy bins one or more of which are closely corresponding and for example substantially identical.

The intensity datasets for transmitted radiation, and for scattered radiation and for example in the preferred case forward scatter radiation and back scatter radiation can be combined to give more detailed information about material composition or to give a more detailed image of the contents or composition of an object. Information may be combined in this way from any combination of datasets across any combination of energy bins. The combination is particularly facilitated where the datasets are resolved into energy bins at least some of which are closely corresponding in extent and for example substantially identical. Thus, the analysis module preferably comprises means to analyse plural energy-resolved datasets together numerically across one or more of the resolved energy bands to derive numerically from such combination analysis information characteristic of the radiation scattering behaviour of the object under test and/or of material(s) comprising an object under test.

Similarly, if the apparatus is further modified for generation of images based on plural energy-resolved datasets, these may comprise combination images made up of a representation of intensity from plural energy-resolved datasets combined across at least some resolved energy bands. The apparatus preferably comprises an imaging module to generate images based on the plural energy-resolved datasets, and in particular to generate such combination images.

It follows by analogy in accordance with a further aspect of the invention that the invention provides:

a method of obtaining radiation interaction data from an object to determine information about the composition of the object comprising the steps of:

provided a radiation source and a radiation detector system spaced therefrom to define a scanning zone therebetween, the detector system having a first and at least one further detector means capable of detecting and collecting information about incident radiation resolvable spectrally across at least a part of the spectrum of the source;

placing an object in and for example causing an object to move relative to and thereby into/through the scanning zone;

positioning the first detector means to collect a first intensity dataset of radiation incident thereupon after transmission through the object and collecting such a dataset;

positioning the at least one further detector means to collect a further intensity dataset of radiation incident thereupon after a scattering interaction with the object and collecting such a dataset;

resolving said first intensity dataset across a plurality of and preferably at least three energy bands within the spectrum of the source and preferably further numerically processing the resolved data to derive therefrom information characteristic of the radiation absorption behaviour of the object under test;

resolving said further intensity dataset across at least three energy bands within the spectrum of the source and preferably further numerically processing the resolved data to derive therefrom information characteristic of the radiation scattering behaviour of the object under test.

Preferably, plural further datasets are collected from plural further detectors, for example including forward scatter and/or back scatter. For some applications it might be desirable to use transmission and forward scatter, for other applications transmission with back scatter and for some applications transmission with forward and back scatter.

Thus, it also follows by analogy that in accordance with a preferred embodiment the invention provides:

a method of obtaining radiation interaction data from an object to determine information about the composition of the object comprising the steps of:

providing a radiation source and a radiation detector system spaced therefrom to define a scanning zone therebetween, the detector system having first, second and third detector means capable of detecting and collecting information about incident radiation resolvable spectrally across at least a part of the spectrum of the source;

placing an object in and for example causing an object to move relative to and thereby into/through the scanning zone;

positioning the first detector means to collect a first intensity dataset of radiation incident thereupon after transmission through the object and collecting such a dataset;

positioning at least one second detector means to collect a second intensity dataset of radiation incident thereupon after a forward scattering interaction with the object and collecting such a dataset;

positioning at least one third detector means to collect a third intensity dataset of radiation incident thereupon after back scattering interaction with the object and collecting such a dataset;

resolving said first intensity dataset across at least three energy bands within the spectrum of the source and preferably further numerically processing the resolved data to derive therefrom information characteristic of the radiation absorption behaviour of the object under test;

resolving said second intensity dataset across at least three energy bands within the spectrum of the source and preferably further numerically processing the resolved data to derive therefrom information characteristic of the radiation scattering behaviour of the object under test;

resolving said third intensity dataset across at least three energy bands within the spectrum of the source and preferably further numerically processing the resolved data to derive therefrom information characteristic of the radiation scattering behaviour of the object under test.

Preferred method features will be inferred by the skilled person analogy with preferred apparatus features described herein and vice versa.

It is the purpose of this present invention to make use of both absorbed and scattered radiation information, preferably including at least one forward scattered mode and for example plural forward scattered and/or back scattered modes as a means of providing a more accurate materials identification capability. Preferably, data is numerically processed in a combined manner from a suitable combination of datasets across a suitable combination of energy bins. The combination is particularly facilitated where the datasets are resolved into closely corresponding energy bins.

The object is to generate intensity datasets from which composition-specific information can be derived numerically, rather than merely to generate data for imaging.

The apparatus thus requires only a simple beam geometry, and for example can be operated with a source collimated to produce a simple pencil beam of incident radiation. The use of a simple apparatus consisting of a collimated pencil beam of x-rays incident upon a single, energy selective detector is all that is required to see how the intensity of the x-ray beam varies with energy when the beam passes through an object. In the preferred case the apparatus comprises a collimator to collimate the source radiation to produce an emitted pencil beam and the method comprises the use of such a beam.

The derivation of composition-specific information is made possible in that a user of the invention is able to collect, by means of a single apparatus and/or in accordance with the foregoing method, and preferably simultaneously or at least closely successively, intensity data both for radiation from the source directly transmitted through the object and for radiation from the source scattered by the object. Moreover, each of these sets of data is resolved into an energy-resolved dataset across at least three energy bands. The resolved datasets may be processed numerically both separately and in combination, for example by combining at corresponding energy bins, to give better material characterisation.

The first detector means of the apparatus of the invention collects transmitted radiation. Further detector means collect scattered radiation from one or more scattering interactions. For example a second detector means detects forward scatter and/or a third detector means detects back scatter. The second detector means is placed so that the detector is at a measurable angle/position from an object-source line to detect forward scatter. This allows intensity data to be collected for a given scatter geometry. This is resolved by the second data processing module across a plurality of energy bands. The third detector means is provided between the x-ray source and the object so that the detector is at a measurable angle/position from the object-source line to detect back scatter. This is resolved by the third data processing module across a plurality of energy bands. The resolved energy bands of the second and third data processing modules largely correspond to the energy bands of the first data processing means.

The energy of the forward scattered photons is given by $E_{ph}=hc/\lambda$ where h is Planck's constant and c is the speed of light. In accordance with the invention, the variation of intensity with wavelength and geometry can be determined for a transmitted or scattered intensity dataset. Material interactions with ionizing radiation are well known and established numerically relationships can be used whereby material composition information can be derived numerically from the energy-resolved dataset.

It should be understood that where reference is made hereinabove to a detector system comprising first and further, and for example first, second and third detector means this suggests no more than that an apparatus in accordance with the invention provides a detection capability in a first position in a direct line with source and object to measure transmitted radiation intensity, and at least one detection capability out of such direct line to measure scattered intensity, for example in the preferred case at least one forward scattered position and more preferably two further detection capabilities out of such direct line to measure scattered intensity at least one forward scattered position and at least one back scattered position.

In particular, there is no requirement for a first and second detector means for detecting the transmitted beam and forward scatter to be physically discrete and separate structures. The invention would also for example encompass a single composite detector system for the first and second detector means in which areas or parts of the composite detector were integrally provided both for detection of directly transmitted and offline scattered radiation. Such a detector could collect both transmitted and forward scattered information simultaneously. Similarly, the invention could encompass a single detector for the first and second detector means which built up both the first and the second dataset closely successively by an appropriate raster scan. What is necessary in such a case is that the apparatus includes, in some form, a means in a direct line with source and object to measure transmitted radiation intensity, at least one further means out of such direct line (and at a measurable angle thereto) to measure forward scattered intensity, and in the preferred case at least one further means out of such direct line (and at a measurable angle thereto) and between the source and the object to measure back scattered intensity. Any third detector means for detecting back scatter will typically be a physically discrete and separate structure.

Similarly, first and further data processing modules, analysis modules etc may be comprised in a single apparatus, in particular to facilitate combined processing of first and further intensity datasets.

As is well understood, both the absorption properties (and hence the transmitted intensity for a given energy) and the scattering behaviour (and hence the intensity collected in the second and third datasets at given forward scatter and back scatter patterns of intensity for a given energy bin) vary systematically and in an manner related to incident radiation energy for different materials according to known physical laws such as those given by example below. The apparatus or method of the invention above described thus collects energy-resolved datasets, both for transmitted intensity via a first detector means, and for scattered intensity via a further detector means, and for example for forward scattered intensity at least one second detector position via a second detector means and for back scatter intensity at least one third detector position via a third detector means, from which it is inherently possible to derive compositional information in accordance with and by application of such known physical laws.

The precise apparatus features and/or methods by which the data is subsequently processed are not specifically limiting to the invention. It is sufficient for the present invention that such energy-resolved data representative of both transmitted and scattered, and for example, forward scattered and back scattered radiation is collected for a single object either simultaneously or closely successively in this manner. Examples of suitable numerical relationships, and of suitable numerical processing algorithms, are given below but do not limit the invention in its broadest scope.

A detector system in accordance with the invention, and/or each of the first and further detector means, may comprise a single linear or area detector or a plurality of discrete detector elements making up a multi-element system. An area detector may be made up of a 2-D array of discrete detector elements and/or of a 2-D array of separately addressable pixels on a compound element. A linear detector may comprise a linear array of discrete detector elements and/or an array of separately addressable pixels on a linear compound element. A detector may be capable of resolving incident radiation spatially so as to collect at least the first and second datasets of intensity information by any combination of inherent spatial resolution as above and raster scanning.

In a preferred embodiment, the detector system comprises at least one linear detector (which term includes a linear detector array) wherein a first portion of the linear detector is in direct line with the source and object under test to collect transmitted information (and constitutes a separately addressable first detector means), and the remainder of the detector is off this direct line so as to collect forward scattered radiation (and is thus a separately addressable second detector means as above defined). The remainder of the detector collects scattered radiation at least one and preferably a plurality of scatter positions and is thus a second detector means as above described. A further, third detector means is preferably provided between the source and the object and out of such direct line between the source and the object (and at a measurable angle thereto) to collect back scattered radiation.

In one possible embodiment the linear detector comprising the first and second detector means extends outwardly from a first position in direct line with the source and object under test in both directions to define such second detector means. In an alternative arrangement a linear detector extends outwardly from the first position in direct line with the source and object under test in one direction only. In either instance, the outwardly extending part of the linear detector preferably comprises a plurality of separately addressable second detector means, for example a plurality of discrete elements or separately addressable areas, from which intensity information can be obtained for a corresponding plurality of scatter positions.

Considering the operation of such a detector, comprising the first and second detector means, in conjunction with the preferred embodiment of source radiation, comprising a source collimated to produce a pencil beam, it can be the seen that the interaction of radiation from the source incident with the object will produce a transmitted intensity, directly related to the absorption characteristics of the object, impinging upon a central first portion of the detector array, with cones of forward scattered radiation extending outwardly therefrom, and separately detectable at various scattered positions by the plural second areas. In the preferred case additionally back scattered radiation extending outwardly back from the object towards the source is separately detectable at various scatter geometries by the single or plural third detector areas.

Alternatively, the same result could be achieved if the detector systems comprising the first and second detector means for measurement of transmission and forward scatter beams comprised an area array of discrete detector elements or separately addressable detector portions with a central area detecting transmitted radiation and areas extending outwardly therefrom detecting forward scattered radiation at various scatter angles.

The radiation source is capable of producing broad spectrum emission over a wide range of energies within a desired operating bandwidth. The radiation source preferably comprises a source to deliver high-energy radiation such as ionizing radiation, for example high energy electromagnetic radiation such as x-rays and/or gamma rays, or subatomic particle radiation, and the detection system is adapted correspondingly to detect radiation in this spectrum. The radiation source for example is a broadband x-ray or gamma-ray source capable of producing broad spectrum emission over a wide range of x-ray or gamma-ray energies.

The source may be a single broad spectrum source across which a plurality of bandwidths or single energies may be identified. For example the source may be a single broad spectrum x-ray source. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

The source is preferably capable of generating a sufficiently broad spectrum of radiation to enable the spectral resolution necessary for the performance of the invention. Preferably the source generates radiation across at least one or more parts of the range of 20 keV to 1 MeV, and more preferably across at least a part, and for example a major part, of the range of 20 keV to 160 keV. For example the source generates radiation ranging across at least one bandwidth of at least 20 keV within the given range. For example the spectrum is such that at least three 10 keV bands can be resolved within that range.

A collimator is preferably provided to produce an emitted beam of suitable geometry from the source. The geometry of the emitted beam will determine the most useful geometry of the detector system. At its simplest, particularly if the apparatus is being used purely to collect spectrally resolved transmission data for the purposes of deriving numerically an indication of mass attenuation coefficient, a simple, effectively one dimensional "pencil" beam may be provided.

The invention exploits the principles of multispectral resolution to gather useful information that can be related to the composition of an object in a scanning zone. The detector system is adapted to generate spectroscopic information about the transmitted or scattered radiation. That is, the detector exhibits a spectroscopically variable response across at least a substantial part of the spectrum of the radiation of the source allowing spectroscopic information to be retrieved. Intensity data over a plurality of energy bands are resolved.

Moreover, instead of merely using this to generate plural band multispectral images of the object, which can give only limited indicative information about composition, the dataset is analysed numerically by processing energy-resolved information to obtain a comparative numerical result that represents in quantified manner a result dataset of data that is more specifically characteristic of an aspect of the composition of the object than could be achieved by a mere multispectral image.

The detector system is adapted to generate spectroscopic information about the transmitted radiation at least to the extent of resolving at least three and more preferably at least five energy bands. It may be convenient to resolve the output into 8 or 16 such energy bands.

So long as at least three specific energy bands are resolved, the bandwidth of each is not directly pertinent to the invention and useful results can be obtained by any suitable approach to dividing the spectrum, either in whole or in part, into separate bands. For example, the entire spectrum or a substantial part thereof may simply be divided between such a plurality of bandwidths, and each data item be considered as a measure representative of intensity across the entire band, and for example an average intensity. Alternatively, a plurality of relatively wide bands, but with discrete gaps therebetween, may be envisaged and analysed on the same basis. Alternatively, "bands" may be narrow even to the point where they essentially approximate to an evaluation of intensity at a single energy. As used herein the concept of intensity at an energy "band" includes evaluation of intensity at such a discrete single energy as well as evaluation of intensity at an energy across a narrow or broad bandwidth. Broad bands may be preferred for transmitted radiation, and narrow bands to identify a particular scatter mode.

It is necessary that the detector systems are enabled to detect radiation in a manner which is spectroscopically resolvable by the data processing apparatus. Preferably, a detector system exhibits a spectroscopically variable response across at least a substantial part of the spectrum of the radiation source allowing detailed spectroscopic information to be retrieved. Preferably, a detector system, or some or all discrete detector elements making up a multi-element system, may be adapted to produce spectroscopic resolution in that it exhibits a direct spectroscopic response. In particular a system or element is fabricated from a material selected to exhibit inherently as a direct material property a direct variable electrical and for example photoelectric response to different parts of the source spectrum.

For example, the detector systems or elements comprise a semiconductor material or materials preferably formed as a bulk crystal, and for example as a bulk single crystal (where bulk crystal in this context indicates a thickness of at least 500 μm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_b Te$ where $a+b<1$ and a and/or b may be zero.

It will be understood that although reference is made herein for convenience to the scanning of an object this should not be considered to limit the application of the invention to the scanning of single homogenous objects. Indeed, for many envisaged applications, an "object" is likely to consist of multiple heterogeneous materials and/or to be a container or other agglomeration of multiple articles, so that any transmitted radiation path is likely to pass through multiple different materials having varied properties. One of the particular advantages of the invention is that it can facilitate resolution of such varied materials.

At its most basic, the invention enables the numerical derivation of an improved indication of identification of materials from collected data based on characteristic transmission/scattering behaviour across different resolved parts of the spectrum. No particular beam geometry is mandated. It is not necessary to generate an image. The invention does not exclude the possibility that the invention forms part of and supplements the information offered by a scanning imaging system, but does not require this extra complexity.

In some instances it may be preferable that the invention forms part of and supplements the information offered by a scanning imaging system. In accordance with this possible embodiment, datasets of information about radiation incidence collected at the detector means are used to generate an image of an object in the scanning zone. In particular, in a possible mode of operation, a combination image is generated combining each dataset resolved spectroscopically across a plurality of frequency bands within the spectrum of the source. If such a mode of operation is desired, an image creation module may be provided to create an image from such intensity datasets, and an image display may be provided to display the image.

Information pertinent to characteristic material data inherent in the transmitted dataset for a given scanning event, and hence the material composition of an object or objects in a transmission path, can be obtained by a single scanning event, for example of a stationary object being scanned by a single beam of appropriate geometry, for example a pencil beam or conical beam. In such circumstance the method merely includes placing the object in a scanning zone to obtain such a single scan and single dataset of data of information about radiation incident at the detector. Such a simple arrangement will often be preferred.

Optionally, the apparatus is adapted to collect in use transmission and scattered intensity data with an object in a single scanning position and for example includes a means to retain an object in a scanning position such as a receptacle into or a platform onto which an object can be placed. Additionally or alternatively it may include a conveyor to convey an object into and out of such scanning position.

In a more complete embodiment of the invention, each of the first and further energy-resolved intensity datasets is processed numerically in association with a suitable relationship by which expected intensity can be related to some aspect of material composition to produce an output result which is indicative of the material composition. In a particularly preferred embodiment, the numerical analysis step of the method, and by analogy the associated module of the apparatus, processes transmitted data and scattered data simultaneously to derive a more accurate indication of composition.

For example, energy-resolved intensity data is processed numerically in such a manner as to allow the extraction from the dataset of a material constant or like characteristic material physical property. Such a material constant or like property may be compared with a suitable data library, for example comprising a library of such data for likely constituent materials, particular target materials etc. Preferably, an apparatus in accordance with this embodiment of the invention comprises a numerical analysis module to effect the said numerical analysis step, a data register comprising such a data library, and a comparator module to effect the comparison step between an output result and data in the data library to establish an indication of material composition.

The invention allows identification of materials from collected and spectrally resolved transmission and scattered data based on a numerical analysis that provides, for example with reference to a suitable data library of characteristic spectrally resolved transmission/scattering data based on equivalent numerical analysis for at least one and preferably a range of target materials and/or objects likely to be encountered in a given application, an indication of material content. The data library may comprise information in any suitable form which can be related in a numerical manner to the product of a numerical analysis of intensity data collected across the resolved energy bands in accordance with the invention. The data library may include standard preset reference materials and/or user input reference materials and/or reference data may be generated from known materials in accordance with the foregoing method. That is, a library of data may be built up by the system, which can in effect "learn" material characteristics, over time. The data library may comprise electronically stored data and/or data stored on a hard medium, such as a printed resource, and may be held and accessed locally and/or remotely, manually and/or automatically, none of which is directly pertinent to this embodiment of the method of the invention.

It will be understood generally that a numerical step in the method of the invention can be implemented by a suitable set of machine readable instructions or code. These machine readable instructions may be loaded onto a general purpose computer, special purpose computer, or other programmable data processing apparatus to produce a means for implementing the numerical step specified, and in particular thereby to produce a calculation means as herein described.

These machine readable instructions may also be stored in a computer readable medium that can direct a computer or other programmable data processing apparatus to function in a particular manner, such that the instructions stored in a computer readable medium produce an article of manufacture including instruction means to implement some or all of the numerical steps in the method of the invention. Computer program instructions may also be loaded onto a computer or other programmable apparatus to produce a machine capable of implementing a computer executed process such that the instructions are executed on the computer or other programmable apparatus providing steps for implementing some or all of the numerical steps in the method of the invention. It will be understood that a step can be implemented by, and a means of the apparatus for performing such a step composed in, any suitable combinations of special purpose hardware and/or computer instructions.

BRIEF DESCRIPTION OF THE DRAWINGS

The invention will now be described by way of example only with reference to the accompanying drawings in which.

DESCRIPTION OF THE PREFERRED EMBODIMENTS

Figure 1:
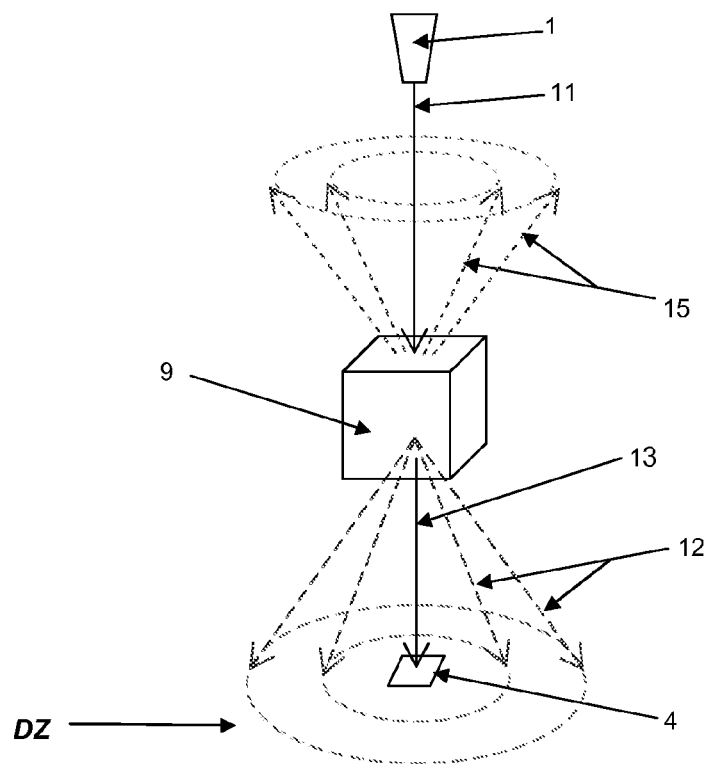
FIG. 1 is a schematic representation of an apparatus in accordance with an embodiment of the invention set up to scan an object and obtain both transmitted and scattered radiation.

Referring to FIG. 1, a suitable x-ray source 1 is used to direct x-rays via a scanning zone in the direction of a detector 4.

The detector 4 comprises material capable of spectroscopic resolution of incident x-rays, and in the specific example comprise cadmium telluride although the skilled person will appreciate that other material selections may be appropriate. To exploit this spectral resolution, the x-ray source 1 emits x-ray across a broad energy spectrum.

The radiation source 1 must produce a distribution of energies across a suitable spectral range for characteristic scattering, and is typically an x-ray source. Tungsten is the most appropriate target, but others could be used.

Alternatively, use may be made of a plural source. In an example this could be an x-ray source collimated to produce a pencil beam with a designed spectrum of operation of around 10 to 50 keV and at least one higher energy radioisotope source, for example at above 100 keV. In the example a 122 keV cobalt-57 source is provided.

Discrete multiple sources and detectors may be provided.

The x-ray source 1 is suitably collimated to produce a primary pencil beam 11. This primary beam 11 is directed at an object 9. A detector apparatus 4 is provided on the opposite side of the object in a detection zone DZ.

Radiation received at the detection zone is affected by interaction with the object in three ways in particular in the illustrated embodiment. First, radiation is absorbed by the object 9, in particular in accordance with equation (1) below, affecting the resultant transmitted beam 13 in a manner which varies characteristically with incident radiation energy.

Second, radiation is forward scattered by materials making up the object 9, in accordance with. Various coherent and incoherent mechanisms, with one or both of Thompson (coherent) scattering and Compton (incoherent) scattering typically predominating. This produces scattering with incident radiation being scattered in a manner characteristic of various material properties for a given material. This is illustrated schematically in the figure by the production of a plurality of scattered "cones" of radiation 12 at characteristic energies and scatter geometries. The result of each scattered cone is a circular footprint at the detection zone DZ. Scattered cones are shown as a means of illustrating the detection of scattered intensity at plural scatter angles in the detection cone DZ, and should not be taken as implying a particular mechanism of scatter that necessarily produces discrete cones of peaks of intensity.

Third, radiation is back scattered, primarily by low atomic number elements making up the material of object 9. The radiation that is back scattered has a characteristic angle of scatter for a characteristic energy (wavelength) of incident radiation for a given material. This is illustrated schematically in the figure by the production of a plurality of scattered "cones" of radiation 15 at characteristic energies and scatter geometries. Again, the presentation of "cones" is for schematic illustrative purpose not intended to imply a particular mechanism of scatter.

Detector systems in accordance with the invention, capable of detecting forward scattered intensity and back scattered intensity resolved into a plurality of energy bins and at a plurality of different angles of forward and back scatter, can generate results from which information indicative of composition of material producing the measured scatter geometry/intensity distribution.

In FIG. 1 a single pixel detector 4 is illustrated in direct transmitted position (that is, serving as a first detector means as hereinbefore defined). Scatter detectors are not shown. At the detection zone level DZ, each illustrated forward scattered cone of radiation presents a circular footprint beyond this central transmitted line. Each illustrated back scattered cone of radiation presents a circular footprint between the radiation source 1 and object 9. Further single pixel detectors at known angles, or a single detector means on an appropriate scanning pattern, can be used to collect back scattered information also.

Figure 2:
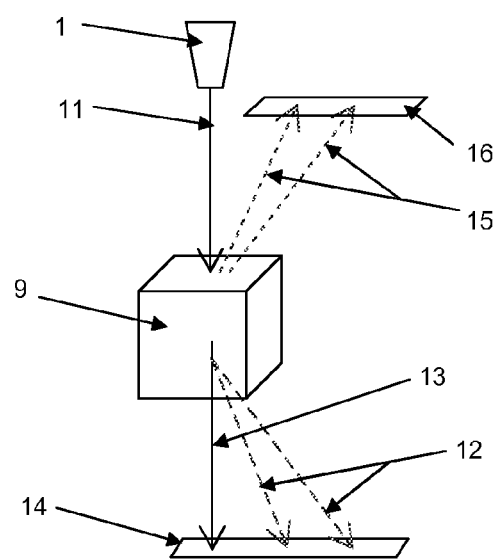
FIGS. 2 and 3 illustrate possible arrangements of linear array detectors.
Figure 3:
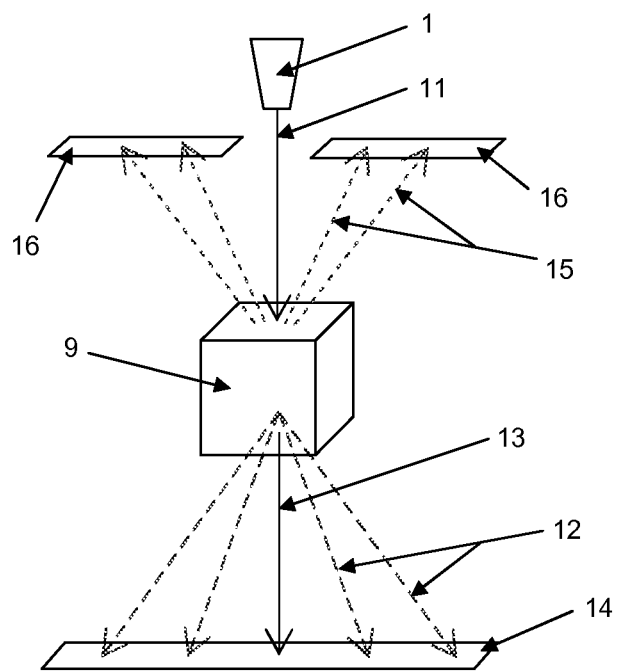

Alternative arrangements are illustrated in FIGS. 2 and 3 for liner array detectors capable of collecting three sets of data simultaneously. In FIG. 2 a linear array detector 14 is positioned so that one end of the array is in line with the primary transmitted beam 13 and detects transmitted intensity, and the remainder of the array extends outwardly at the detection zone level to detect scattered beams 12 at a plurality of different scattered angles. A further linear array 16 is positioned in a region between the radiation source 1 and the object and clear of a line between the source and the object 9 to detect scattered beams 15 at a plurality of different scattered angles.

In FIG. 3, in an alternative arrangement, the linear array 14 is centred on the transmitted beam 15 and extends outwardly in both directions to detect scattered beams 17 at a plurality of different scattered positions. Further linear arrays 16 are positioned in a region between the source 1 and the object 9 with sufficient clearance between the arrays 16 for the incident beam 11 to pass from the source to the object. The detectors 16 detect scattered beams 15 at a plurality of different scattered positions.

Figure 4:
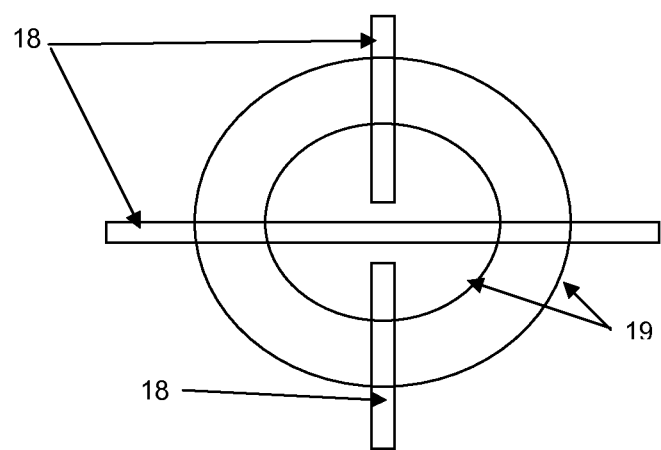
FIG. 4 illustrates in plan view a possible arrangement in a detection zone for detection of transmitted and forward scattered radiation.

A particularly preferred arrangement for detecting transmitted and forward scattered beams is represented in FIG. 4, in which two linear array detectors 18 are arranged orthogonally at a scanning footprint level to pick up information from the characteristic forward scattered radiation circles 19 in the manner shown.

Figure 5:
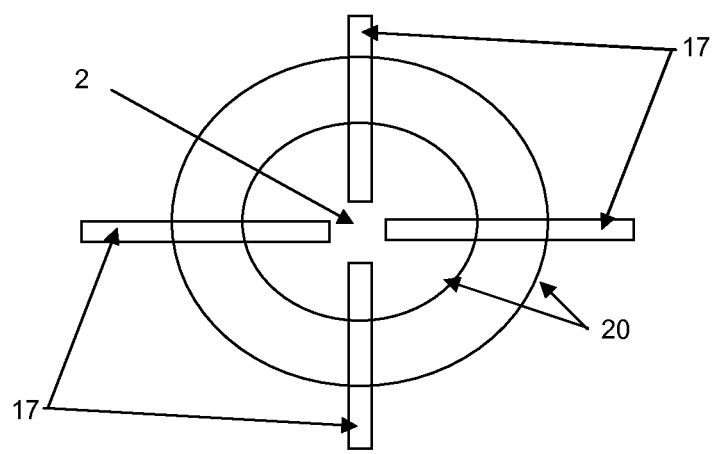
FIG. 5 illustrates in plan view a possible arrangement in a detection zone for detection of back scattered radiation.

A particularly preferred arrangement for detecting back scattered beams is represented in FIG. 5, in which four linear array detectors 16 are arranged orthogonally at a scanning footprint level to pick up information from the characteristic back scattered radiation circles 20 in the manner shown. Clearance is provided in region 2 for the incident beam to pass from the source to the object.

Figure 6:
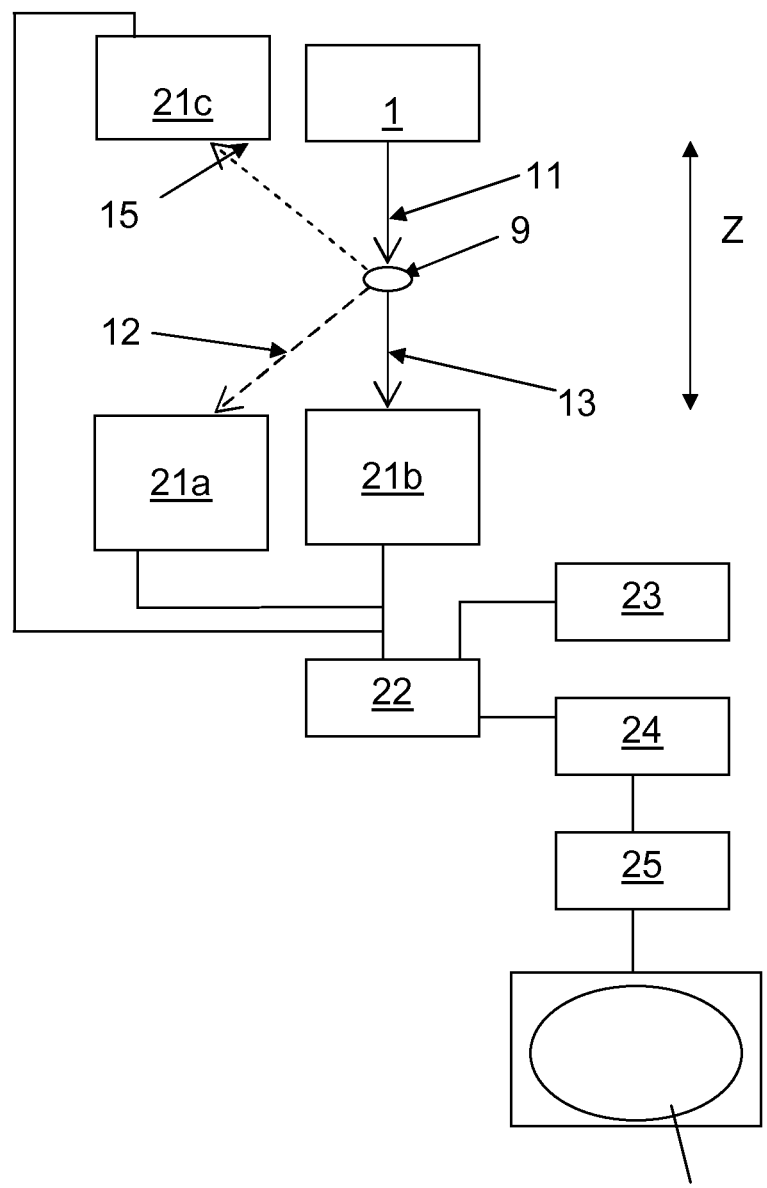
FIG. 6 is a schematic representation of a data processing apparatus in accordance with an embodiment of the invention.

A general schematic representation of the resolution of the data collected by the above apparatus is presented in FIG. 6. An x-ray source 1 and laterally spaced detector in the form of first detector means 21a and second detector means 21b together with a further detector 21c define a scanning zone Z between them. In use, an object to be scanned is brought into the scanning zone in the usual manner, for example placed on a suitable object platform or conveyed via a suitable conveyor.

In the illustrated example, a sample of material 9 sits in the scanning zone Z. An incident beam 11 from the x-ray source is illustrated. A forward scattered beam 12 is scattered by a suitable mechanism, which might for example be incoherent Compton scattering, and is incident upon a first detector means 21a. The transmitted beam 13 is incident upon a detector means 21b. A back scattered beam 15 is incident upon a detector means 21c. Detector means in the preferred embodiment comprises linear arrays of cadmium telluride detector units.

The detector arrays 21a, b, c are in data communication with a processor 22. The detector arrays are used to generate a dataset of intensity information in familiar manner. The inherent spectral resolution of the material in the arrays allows the processor 22 to resolve this dataset differentially across a plurality of pre-set frequency/energy bands in accordance with the principles of the invention by reference to energy band boundaries stored in the data register 23.

Figure 7:
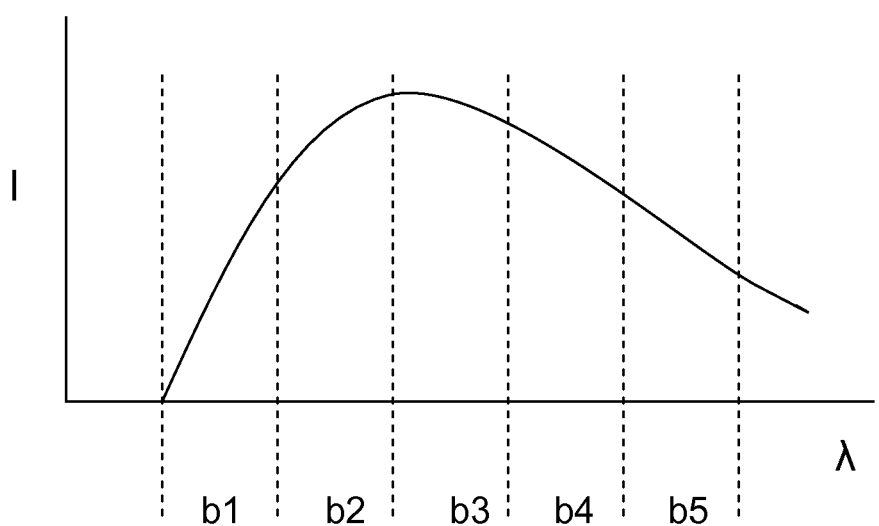
FIG. 7 shows the source spectrum and energy bands for data processing in accordance with an embodiment of the invention.

The source 1 generates x-rays across a relatively broad spectrum of energy, so that this resolution may be exploited. The source 1 is preferably tungsten source, which gives a characteristic plot of x-ray intensity (I) versus wavelength ($\lambda$) as is illustrated in FIG. 7. FIG. 7 illustrates how this spectrum might be divided to operate a system in accordance with the principles of the invention into successive relatively broad bands b1 to b5.

A calculation module 24 performs a numerical analysis in accordance with the general principles of the invention making use of known physical relationships that relate intensity variation to initial radiation energy spectrum for the variety of radiation interaction processes that affect the transmitted and scattered intensities in a manner that varies spectroscopically. These known relationships can be used to generate characteristic materials property data from which it is possible to derive information pertinent to material composition with reference to previously stored reference data in the data register 25. The resultant data so generated may be identified to a user of the scanning system in any suitable way, for example via the display 27 or by another suitable alerting system. Any of the data processing or storage elements of the apparatus, for example including one or more of the processor 22, data register 23, calculation module 24 and data register 25, may be provided by a suitably programmed data processor means such as a special purpose or general purpose computer.

A first dataset of transmitted intensity information is generated by resolving, at least to some extent, a relationship between incident energy/wavelength and transmitted intensity derived at a detector, or that part of a detector array, in direct line with source and object for numerical analysis in accordance with the principles of the invention. This data may be numerically analysed with reference to a suitable numerical relationship known to relate transmitted to incident intensity, in particular one which relates to photoelectric absorption.

A second dataset of forward scattered intensity information is generated by resolving, at least to some extent, a relationship between incident energy/wavelength and intensity derived at a detector, or that part of a detector array, away from direct line for numerical analysis in accordance with the principles of the invention. This data may be numerically analysed with reference to a suitable numerical relationship known to relate forward scattered to incident intensity, in particular one which relates to Thompson (coherent) scattering or Compton (incoherent) scattering effects, A third dataset of back scattered intensity information is generated by resolving, at least to some extent, a relationship between incident energy/wavelength and intensity derived at the detector 21c in accordance with the principles of the invention. This data may be numerically analysed with reference to a suitable numerical relationship known to relate back scattered to incident intensity.

The respective energy-resolved datasets may be analysed numerically separately or together to generate composition correlatable information.

Some possible embodiments of the invention involving suitable numerical analysis of frequency-specific datasets based on an intensity ratio analysis to obtain a frequency-comparative dataset of quantified information correlatable to composition will now be described in more detail. It will be appreciated that these are examples only and that the principle of the invention is applicable to any numerical analysis technique that will yield quantified information correlatable to composition as a means of obtaining useful data from a multispectral resolved dataset as an alternative to that which could be obtained from an image alone.

In a possible numerical analysis of the first dataset, an energy-resolved dataset is derived that comprises at least data about intensity of transmitted radiation at a plurality of energy bands, and for example comprises data representative of the average intensity of transmitted radiation across a given band or at least a sufficiently representative part thereof. A numerical analysis is carried out of at least one such pair of datasets to produce a comparative dataset preferably by applying a comparative function to at least one pair of energy-specific intensity datasets and especially average intensity datasets. More preferably yet the numerical analysis step comprises determining an intensity ratio, and for example an average intensity ratio (that is, a ratio of average intensities across a given energy band or at least a part thereof as previously defined), for at least one pair of energy-specific datasets.

Intensity ratios can represent a particularly useful quantification of the dataset of transmitted radiation that can be particularly characteristic of specific material composition.

Appropriate and where applicable different numerical weighting factors may be applied to data in different frequency-specific datasets prior to or as part of the process of any numerical comparison therebetween to produce a suitably modified/meaningful result dataset without departing from the principle of the invention. Such weightings might for example correct for intensity variations in a given source spectrum, for noise of any kind, or for any other factor that it might be desirable to account for to improve the numerical result.

Transmitted intensity may be described by a mass attenuation relationship such as the Beer-Lambert Law:—

$$I/Io = \exp[-(\mu/\rho)\rho t] \quad (1)$$

Where $\mu/\rho$=Mass attenuation coefficient, a material constant which is characteristic of the weighted elemental composition of a material
I=Final intensity
Io=Initial intensity
$\rho$=density of the material
t=thickness of the material The first detector means of the apparatus of the invention is placed so that detector is in line with an object-source line to collect transmitted radiation. This allows intensity data to be collected and resolved by the first data processing module across at a plurality of energy bands from which material composition information can be derived numerically from the energy-resolved dataset by application of this law in some suitable manner.

Accordingly, the method preferably comprises a method applying a mass attenuation relationship such as equation (1) above, for example; evaluating the ratio between intensity data items for at least two pairs of energy bands in a given intensity dataset and for example each successive such energy band to obtain a numerical indicator in functional relationship with a mass attenuation coefficient associated with the intensity dataset;

comparing the same with a library of data indicative of characteristic mass attenuation coefficients, and in particular for example with mass attenuation coefficients characteristic of target materials such as suspect materials, in order to obtain an indication of the likely material content of material in a transmission path producing such intensity dataset.

By analogy in this embodiment a suitable apparatus comprises: a calculation means to evaluate the ratio between intensity data items for at least two pairs of energy bands in a given intensity dataset and for example each successive such energy band to obtain a numerical indicator in functional relationship with a mass attenuation coefficient associated with the intensity dataset; and preferably further a further data register to store such numerical indicator;

a data library of data indicative of characteristic mass attenuation coefficients and in particular for example with mass attenuation coefficients characteristic of target materials such as suspect materials;

a comparator to compare the numerical indicator with data in the library and derive therefrom an indication of the likely material content of material in a transmission path producing the said intensity dataset.

In accordance with the embodiment, for each such scanning event, ratios of at least two pairs of such resolved intensity data item measurements, and for example successive intensity data item measurements, are obtained numerically, to provide representative information which can be correlated to the mass attenuation coefficient necessary to produce such an intensity pattern. Most of the variables associated with a given scanning event are constant with respect to the frequency/energy of the incident radiation from the source. However, the mass attenuation coefficient varies with energy in characteristic way. By performing such a ratio analysis on intensity data across at least three different energy bands for a given scanning event to generate at least two ratios, data which is representative of the functional relationship between mass attenuation coefficient and incident radiation energy can be obtained. Thus, inferences relating to the specific mass attenuation coefficient applicable to the transmission path through material under test for a given scanning event can be drawn. A comparison is then made to a suitable database of data representative of the mass attenuation coefficient for different materials and/or target objects to give a more representative indication of what is being scanned.

One of the simplest ways to eliminate the additional terms is to take a ratio of the transmission at different energies and for example a ratio of successive readings at a plurality of successive different energies. It can be seen that a ratio will in principle eliminate the material thickness and density as constant terms. This will therefore make the mass attenuation coefficient the only remaining term that will affect the transmission ratio.

Preferably a comparison is made to a library of results. Thus, preferably, the apparatus further comprises one or more of:

a further data register to store such comparative data; a data library of known data for known materials; and a comparator to compare the comparative data in the data register with data in the library and derive therefrom an indication of the likely material content of material in a transmission path.

The apparatus of the invention has a calculation means that effects a comparison between at least one pair of energy-specific datasets at least by applying a comparative function to at least one pair of frequency-specific intensity datasets to determine an intensity ratio for at least one pair of frequency-specific datasets to produce a frequency-comparative dataset. The apparatus optionally further has a comparator to compare the frequency-comparative data in the data register with data in a library. Any suitable form of calculation means and/or comparator and/or library combining suitable hardware and software and combining automatic and user-input calculation steps can be envisaged. For example a calculation means and/or comparator and/or library comprises a suitably programmed data processing apparatus such as a suitably programmed general purpose or special purpose computer.

Under certain circumstances use of a mass attenuation absorption relationship can break down due to excessive scattering of the beam as opposed to the absorption of it. This scattered information is lost in a simple apparatus that merely identifies transmitted intensity and it can have the effect of hindering the materials identification process.

The invention exploits the fact that the scattering events are also generally characteristic of the material under test according to known relationships.

Figure 8:
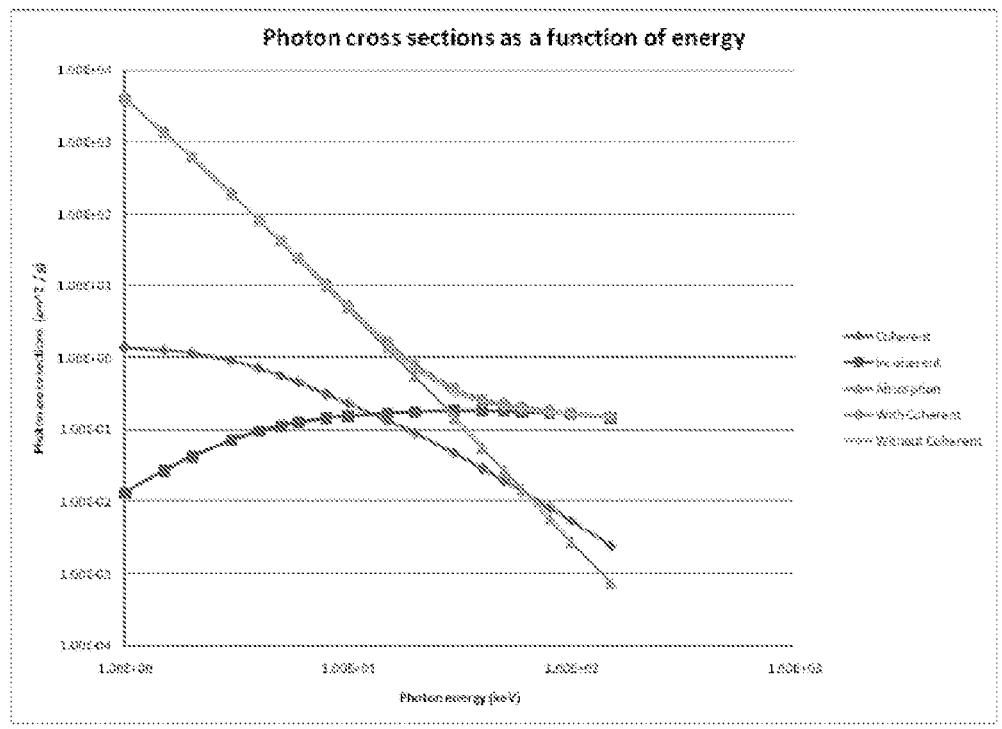
FIG. 8 shows a photon cross-section for water as a function of energy comparing the effects of the photoelectric effect, Thompson (coherent) scattering and Compton (incoherent) scattering.
Figure 9:
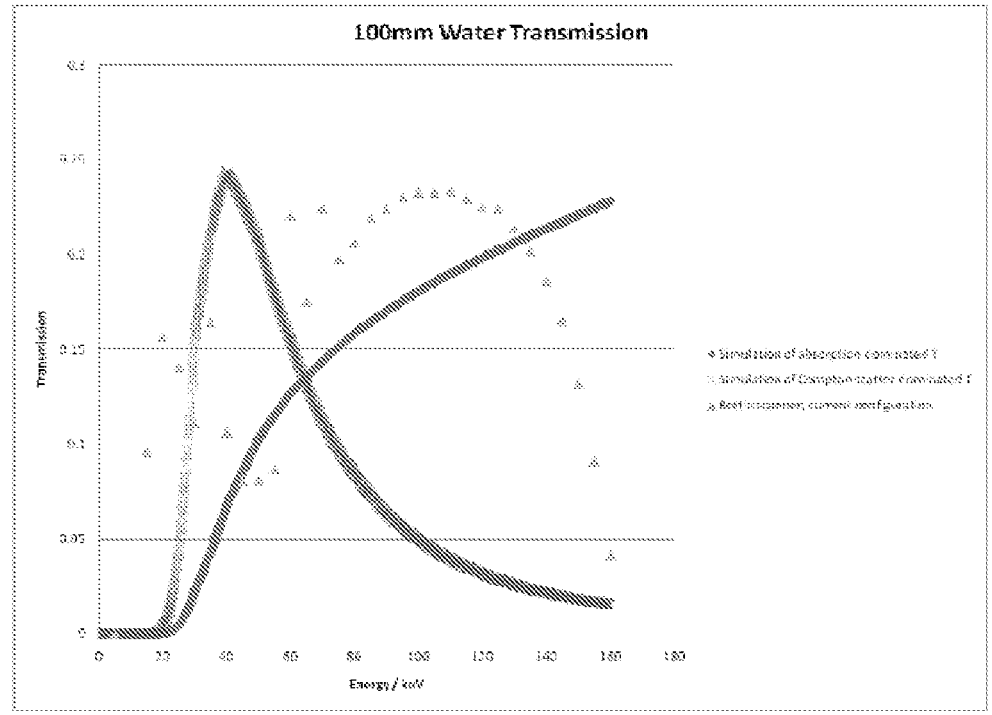
FIG. 9 shows transmission curves for 100 mm water.

FIGS. 8 and 9 illustrate the principles to be exploited in detecting and processing for transmission, coherent and incoherent scatter. In the general case, for photons with energy of between 10 keV and 160 keV the main contributing physical processes are the photoelectric effect, Thompson (coherent) scattering and Compton (incoherent) scattering. The relative magnitudes of the scattering cross sections are illustrated for water in FIG. 8 (note that this is a Log: Log plot). There is a transition between photoelectric and Compton scatter dominated processes at 30 to 40 keV (higher for heavier elements, e.g. 60 keV for HCl). By probing this transition we can discover more about the material properties. Broadly speaking the photoelectric effect is dominated by the atomic number (Z) and so is sensitive to the elemental composition of the material. Compton scatter is dominated by the number of electrons in the beam path and so is sensitive to the physical density of the material.

In electron and optical microscopy subtle differences in material properties are often exposed through dark field techniques. The main, straight through, beam is stopped (typically via lensing or mechanical beam stops) and the image contrast is dominated by scattered or diffracted radiation. An analogous method for a system such as embodied by the present invention might be to switch the configuration from absorption dominated to scatter dominated contrast.

The curve in FIG. 9 is a calculation of the normalised transmission (I/Io). As one might expect the transmission increases as the photoelectric interaction mean free path increases with energy. The purple curve exaggerates the impact of Compton scatter on the transmitted intensity by arbitrarily increasing the Compton scatter cross section. The green curve is the scatter dominated output of a typical experimental liquid scanner.

There are several ways in which the contrast mechanism can be adjusted to suit the measurement or multiple contrast mechanisms can be selected in sequence. In a basic layout such as illustrated above it is possible to use a plurality of detectors to inform of the distribution of scattered radiation. For instance, for a cylindrically collimated beam, a detector or separately addressable portion thereof may be provided on the main system axis and another detector or separately addressable portion thereof may be provided off axis. Since the signal from the former will be absorption dominated and the latter scatter dominated, a differential analysis would provide a useful insight on the material properties. This scheme might be extended as above described to linear or 2 dimensional arrays of detectors as above described for better mapping of the intensity distribution. The general schematic might be further refined by the use of detector collimators for preferentially selecting primary (direct) or secondary (scattered) photons. Alternatively individual detectors or combinations of detectors or separately addressable areas of detectors might be selected by electronic or software switching to de-convolute the scattered and transmitted photon signals.

These examples illustrate the principle of the invention, whereby spectrally resolved transmission/scattering data is collected in a manner that may be utilised in a numerical analysis that provides potential for a better identification of materials present.

The invention claimed is:

1. An apparatus for obtaining radiation interaction data from an object to determine information about the composition of the object comprising:
    a radiation source configured to produce a single pencil beam of radiation;
    a radiation detector system spaced therefrom to define a scanning zone therebetween and to collect in use information about radiation incident at the detector system after interaction with an object in the scanning zone, the detector system configured to detect and collect spectroscopically resolvable information about incident radiation; and
    means to retain an object in a stationary scanning position within the scanning zone;
    wherein the radiation detector system comprises a first detector means positioned to collect a first intensity dataset of radiation incident thereupon that results from the single pencil beam of radiation after transmission through an object, and at least one further detector means positioned to collect a further intensity dataset radiation incident thereupon that results from the single pencil beam of radiation after a scattering interaction with an object;
    wherein the apparatus further comprises a first data processing module adapted to resolve said first intensity dataset across at least three energy bands within the spectrum of the source, and at least one further data processing module adapted to resolve said further intensity dataset across at least three energy bands within the spectrum of the source including determining the scatter angle that results from the single pencil beam of radiation; and
    wherein the radiation detector system comprises a linear detector and wherein the first detector means is a first portion of the linear detector that is in direct line with the source and object under test to collect transmitted information and the at least one further detector means is a second portion of the linear detector which is located off the direct line so as to collect forward scattered radiation.

2. An apparatus in accordance with claim 1 comprising a further detector means positioned to collect a further intensity dataset of radiation incident thereupon after backward scattering interaction with an object.

3. An apparatus in accordance with claim 1 wherein each data processing module is adapted to resolve its respective intensity dataset across at least some closely corresponding energy bands.

4. An apparatus in accordance with claim 1 wherein each data processing module further comprises an analysis module to analyze the energy-resolved data across at least some of the resolved energy bands and to derive numerically therefrom information characteristic of the radiation absorption behavior of an object under test and/or of material(s) comprising an object under test.

5. An apparatus in accordance with claim 4 wherein the analysis modules comprise means to analyze plural energy-resolved datasets together numerically across at least some resolved energy bands to derive numerically from such combination analysis information characteristic of the radiation scattering behavior of an object under test and/or of material(s) comprising an object under test.

6. An apparatus in accordance with claim 1 wherein the second portion of the linear detector extends outwardly from the first portion in both directions.

7. An apparatus in accordance with claim 1 wherein the detector system comprises two orthogonal linear detectors, each having a first portion and a second portion.

8. An apparatus in accordance with claim 1 further comprising a further detector provided between the source and the object and out of such direct line between the source and the object to collect back scattered radiation.

9. An apparatus in accordance with claim 1 wherein the radiation source comprises a source to deliver high-energy radiation selected from high energy electromagnetic x-rays and/or gamma rays and subatomic particle radiation, and the detection system is adapted correspondingly to detect radiation in this spectrum.

10. An apparatus in accordance with claim 1 further comprising a collimator to collimate the source radiation to produce an emitted pencil beam.

11. An apparatus in accordance with claim 1 wherein the detector system is fabricated from a material inherently capable of exhibiting a spectroscopically variable response across at least part of the spectrum of the source.

12. An apparatus in accordance with claim 11 wherein the detector comprises a semiconductor material selected from cadmium telluride, cadmium zinc telluride (CZT), cadmium manganese telluride (CMT), germanium, lanthanum bromide, and thorium bromide.

13. An apparatus in accordance with claim 11 wherein the detector comprises a semiconductor material or materials formed as bulk crystal including a Group II-VI semiconductor material.

14. An apparatus in accordance with claim 1 wherein the means to retain an object in a scanning position comprises a receptacle into or a platform onto which an object can be placed.

15. A method of obtaining radiation interaction data from an object to determine information about the composition of the object comprising the steps of:
    providing a source of a single pencil beam of radiation and a radiation detector system spaced therefrom to define a scanning zone therebetween, the detector system having a first and at least one further detector means configured to detect and collect information about incident radiation that results from the single pencil beam of radiation resolvable spectrally across at least a part of the spectrum of the source, the radiation detector system comprises a linear detector and wherein the first detector means is a first portion of the linear detector that is in direct line with the source and object under test to collect transmitted information and at least one further detector means is a second portion of the linear detector which is located off the direct line so as to collect forward scattered radiation;
    placing an object in under test into the scanning zone and holding the object stationary to be scanned by the single pencil beam;

positioning the first portion of the linear detector to collect a first intensity dataset of radiation incident thereupon that results from the single pencil beam of radiation after transmission through the object and collecting such a dataset;

positioning the second portion of the linear detector to collect a further intensity dataset of radiation incident thereupon that results from the single pencil beam of radiation after a scattering interaction with the object and collecting such a dataset;

resolving said first intensity dataset across at least three energy bands within the spectrum of the source; and resolving said further intensity dataset across at least three energy bands within the spectrum of the source and determining the scatter angle that results from the single pencil beam of radiation.

16. A method in accordance with claim 15 comprising positioning a further detector means to collect a further intensity dataset of radiation incident thereupon after backward scattering interaction with the object.

17. A method in accordance with claim 15 comprising the further step of numerically processing the resolved data of each intensity dataset to derive therefrom information characteristic of the radiation absorption and/or scattering behavior of the object under test.

18. A method in accordance with claim 17 wherein each resolved intensity dataset is processed numerically in association with a suitable relationship by which expected intensity can be related to some aspect of material composition to produce an output result which is indicative of the material composition.

19. A method in accordance with claim 18 wherein transmitted data and scattered data are simultaneously processed numerically to derive a more accurate indication of composition.

20. A method in accordance with claim 15 wherein the step of holding the object stationary comprises placing the object in or on a means to retain an object in a stationary scanning position in the scanning zone.

21. A method in accordance with claim 20 wherein the means to retain an object in a scanning position comprises a receptacle into or a platform onto which an object can be placed.

* * * * *